United States Patent [19]
Toraya et al.

[11] Patent Number: 5,510,479
[45] Date of Patent: Apr. 23, 1996

[54] HYDROPHOBIC VITAMIN $B_{12}$ DERIVATIVES

[75] Inventors: Tetsuo Toraya; Mamoru Yamanishi, both of Okayama; Yusuke Takahata, Kita-Kanbara; Ichiro Kojima, Yokosuka, all of Japan

[73] Assignee: Nippon Oil Company, Tokyo, Japan

[21] Appl. No.: 248,810

[22] Filed: May 25, 1994

[30] Foreign Application Priority Data

May 27, 1993 [JP] Japan ................... 5-126257

[51] Int. Cl.$^6$ ............ C07H 23/00; A61K 31/68
[52] U.S. Cl. ........................ 536/26.4; 540/474
[58] Field of Search ................ 540/145, 452; 536/26.4

[56] References Cited

U.S. PATENT DOCUMENTS

| | | | |
|---|---|---|---|
| 2,967,860 | 1/1961 | Perlman et al. | 536/26.4 |
| 2,984,661 | 5/1961 | Nomine et al. | 260/211.5 |
| 5,405,839 | 4/1995 | Toraya et al. | 536/26.4 |

FOREIGN PATENT DOCUMENTS 0005834  12/1979  European Pat. Off. ........ C07H 23/00

OTHER PUBLICATIONS

Toraya, T. et al. "Preparation, Properties and Biological Activities of Succinyl Derivatives of Vitamin B12," *Chemical Abstracts* 83(11): p. 638, col. 1, 1975.

*Primary Examiner*—Mukund J. Shah
*Assistant Examiner*—Pavanaraty R. Sripada
*Attorney, Agent, or Firm*—Seed and Berry

[57] ABSTRACT

A novel hydrophobic vitamin $B_{12}$ derivative represented by the formula:

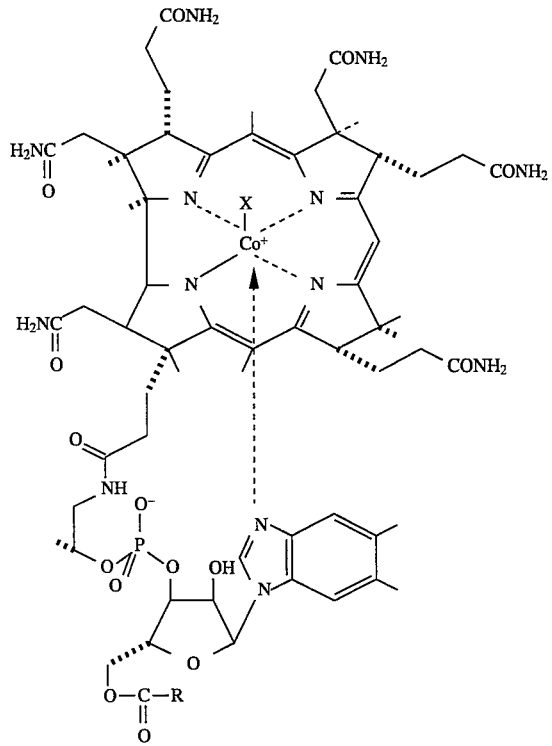

wherein R represents an alkyl group having 2 to 17 carbon atoms, and X represents a cyano group, a hydroxyl group, an alkyl group or a 5'-deoxyadenosyl group. Since the derivative is hydrophobic, it can be taken up by an organism by thermodynamic diffusion, a passive transport, without an active transport.

1 Claim, 3 Drawing Sheets

× CN-B$_{12}$

● CN-B$_{12}$ (C$_9$CO)

◇ CN-B$_{12}$ (C$_7$CO)

◉ CN-B$_{12}$ (C$_{11}$CO)

○ CN-B$_{12}$ (C$_{17}$CO)

HYDROPHOBIC VITAMIN $B_{12}$ DERIVATIVES

BACKGROUND OF THE INVENTION

1. Field of the Invention

The present invention relates to vitamin $B_{12}$ derivatives having enhanced hydrophobicity. The vitamin $B_{12}$ derivatives are useful as a component of pharmaceutical compositions, foods, feeds and the like.

2. Related Art

As analogues of vitamin $B_{12}$, cyanocobalamin, hydroxocobalamin, adenosylcobalamin, methylcobalamin and the like are known. However all of them are water soluble substances, and on an oral administration are taken up at a lower portion of the small intestine and a terminal portion at 50 cm of the ileum, by the action of an intrinsic factor in gastric fluid (VITAMIN SCIENCE II, physiological activities of vitamin $B_{12}$, page 554, 1980, Tokyo Kagaku Dojin). Vitamin $B_{12}$ is taken up by active transport, and vitamin $B_{12}$ deficiency diseases are, in many cases, caused by a disorder of this uptake mechanism.

Since known vitamin $B_{12}$ analogues are water soluble, their affinity for tissues is low, and in the case where the uptake mechanism is in disorder, they cannot be taken up by diffusion as an alternative uptake mechanism. Accordingly, it is desired to develop vitamin $B_{12}$ derivatives which can be taken up by diffusion.

On the other hand, where vitamin $B_{12}$ is added to a blended feed, it may be easily dissolved in water and removed. It is desired to develop hydrophobic vitamin $B_{12}$ derivatives capable of exhibiting its native biological activities.

DISCLOSURE OF THE INVENTION

Accordingly, an object of the present invention is to provide hydrophobic vitamin $B_{12}$ derivatives. The object is accomplished by providing hydrophobic vitamin $B_{12}$ derivatives having an acyl group bonded to the sugar moiety of the lower ligand.

The hydrophobic vitamin $B_{12}$ derivatives of the present invention are easily taken up by thermodynamic diffusion without using the nomal uptake mechanism by active transport, and after the uptake, the acyl group is cut off from vitamin $B_{12}$ derivative to liberate vitamin $B_{12}$, while the liberated acyl group is harmless to organisms. Accordingly, hydrophobic vitamin $B_{12}$ of the present invention allows the uptake of vitamin $B_{12}$ in the case of vitamin $B_{12}$ deficient diseases caused by disorder of the uptake mechanism.

DETAILED DESCRIPTION OF THE INVENTION

Vitamin $B_{12}$ derivatives of the present invention are represented by the following formula:

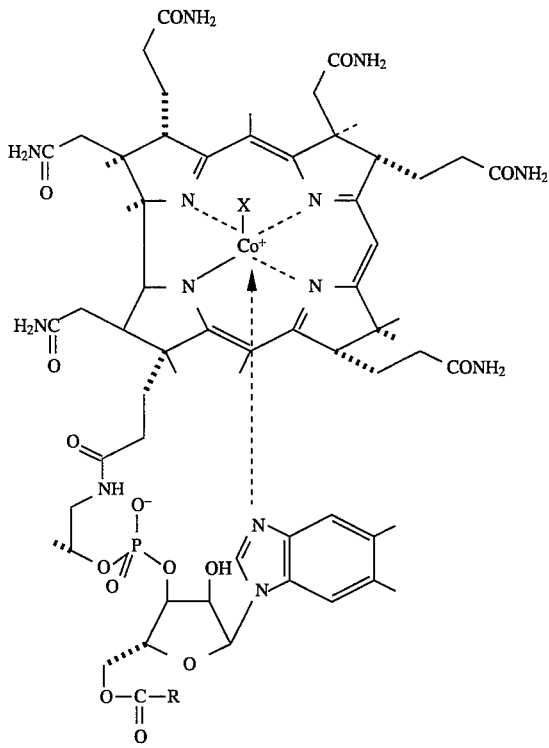

wherein R represents an alkyl group having 2 to 17 carbon atoms, and X represents a cyano group, a hydroxyl group, an alkyl group or a 5'-deoxyadenosyl group. In the present vitamin $B_{12}$ derivatives, as the substituent group RCO of the lower ligand, an acyl group having 3 to 18 carbon atoms preferably is used. Here, the lower ligand means one of the two ligands coordinating from an axial direction to the cobalt, which positions at the fifth coordinate site (side of the base, 5,6-dimethylbenzimidazole).

Where the number of carbon atoms of the acyl group is less than 3, sufficient hydrophobicity of the vitamin $B_{12}$ derivative is not provided, while if the number of carbon atoms is more than 20, the resulting vitamin $B_{12}$ is insoluble in water.

The alkyl group for X has up to 25 carbon atoms, and is for example a lower alkyl group such as methyl, ethyl, propyl or butyl, etc.

A vitamin $B_{12}$ derivative of the present invention can be produced, for example, by reacting cyanocobalamin with an carboxylic anhydride having a desired number of carbon atoms to obtain a cyano(5'-O-acyl)cobalamin.

The hydrophobicity of the present vitamin derivative can be expressed by various ways, including an Rf value in thin layer chromatography (TLC), a partition ratio between water and an organic solvent, or the like.

The relationship between the number of carbon atoms in the acyl group RCO and Rf values in TLC is as follows. Note that in the present invention, cyanocobalamin is shown by "$CN-B_{12}$", and cyano(5'-O-acyl)cobalamin is shown as "$CN-B_{12}(CnCO)$", wherein n is the number of carbon atoms of R in the acyl group RCO.

TABLE 1

| Vitamin $B_{12}$ derivative | Solvent | |
| --- | --- | --- |
| | WSB | B/P/W |
| CN—$B_{12}$ | 0.062 | 0.22 |
| CN—$B_{12}(C_2CO)$ | 0.072 | 0.26 |
| CN—$B_{12}(C_7CO)$ | 0.167 | 0.43 |
| CN—$B_{12}(C_8CO)$ | 0.174 | 0.44 |
| CN—$B_{12}(C_{11}CO)$ | 0.181 | 0.45 |
| CN—$B_{12}(C_{17}CO)$ | 0.200 | 0.46 |

WSB: 2-Butanol saturated with water B/P/W: 1-Butanol/2-propanol/water=10/7/10

The above result represented in Table 1 shows that the hydrophobicity of vitamin $B_{12}$ derivatives increases as the number of carbon atoms in R increases.

Figure 1:
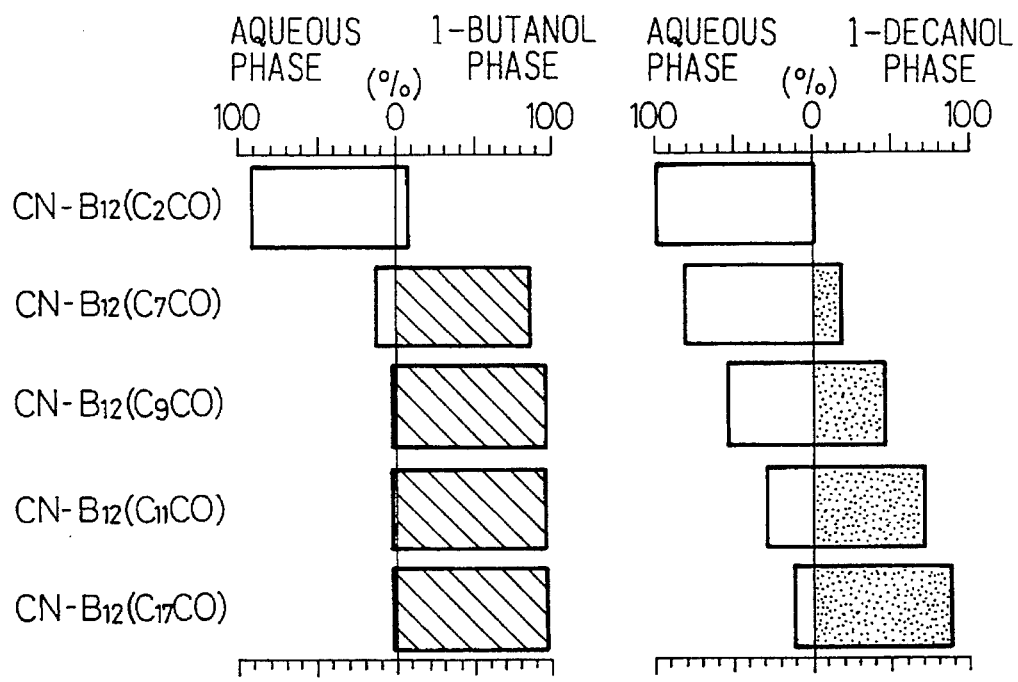
FIG. 1 represents the partition ratios of various vitamin $B_{12}$ derivatives of the present invention between water and an organic solvent.

FIG. 1 shows the distribution ratios of various vitamin $B_{12}$ derivatives between water and one of some organic solvents. Note that this result was obtained by adding the same volumes of water and an organic solvent to a vitamin $B_{12}$ derivative to be tested, measuring absorbance (546–550 nm) of each phase, and calculating a ratio thereof.

EXAMPLES

Here, the present invention is further explained by Examples, which do not limit the scope of the present invention thereto.

EXAMPLE 1

Synthesis and purification of CN-$B_{12}(C_{11}CO)$

First 15 μmoles of cyanocobalamin was dissolved in 5 ml of dry DMSO/DMF (1:1).

To the resulting solution was added 1.6 mmoles of dodecanoic anhydride, and after stirring at 42° C. for 23 hours, 10 ml of diethyl ether and 10 ml of water were added thereon to terminate the reaction.

Next, 25 ml of the reaction mixture was put into a separating funnel, 40 ml of ethyl ether and 40 ml of water were further added thereon, and the mixture was shaken to extract CN-$B_{12}(C_{11}CO)$. The aqueous layer was washed three times with diethyl ether, and concentrated by an evaporator. The resulting concentrate was subjected to a column chromatography on XAD2, and after eluting unreacted cyanocobalamin with water, CN-$B_{12}(C_{11}CO)$ was eluted with 50% 2-methyl-2-propanol. The resulting fraction was dried into a solid by an evaporator, which solid was then dissolved in 2 ml of methanol. The solution was subjected to paper chromatography (developing solvent: 1-butanol/2-propanol/water (10:7:10)), and the part of the paper containing the main band was cut out, and the main band was eluted with 50% 2-methyl-2-propanol.

The eluate was purified by a high performance liquid chromatography (mobile phase: 62% methanol; column: ODS), dried into solid in an evaporator, and the solid was dissolved in 30% ethanol and the resulting solution was stored at −80° C.

Figure 2:
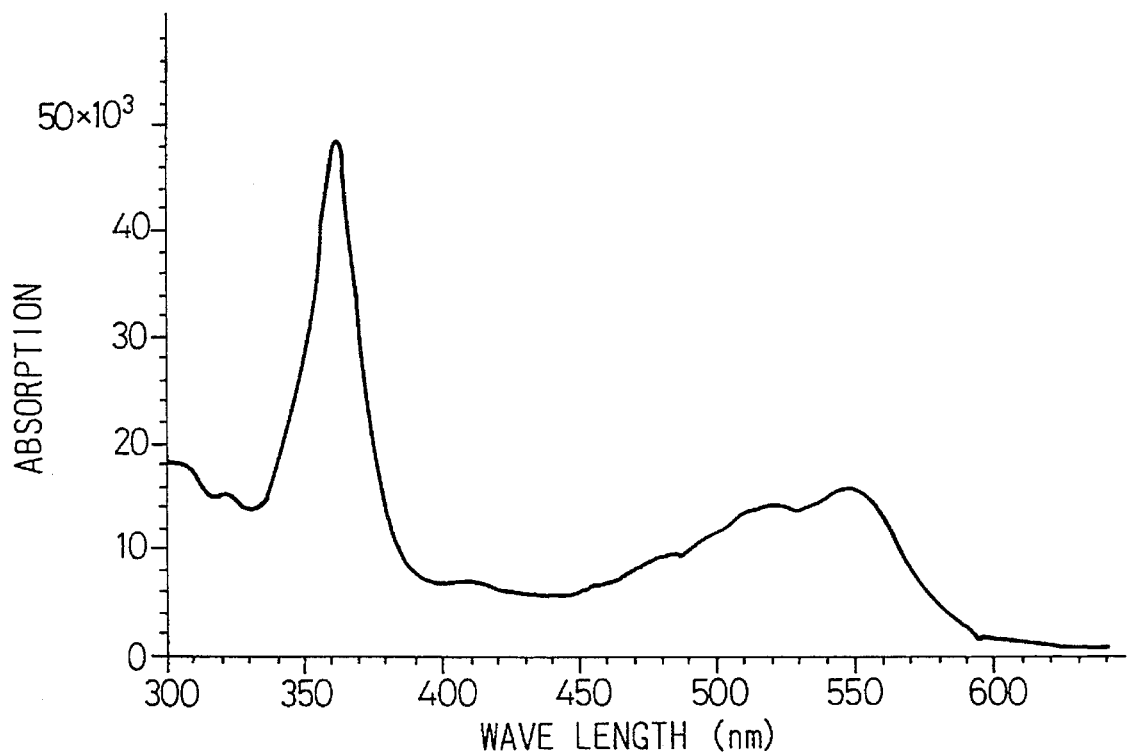
FIG. 2 represents an absorption spectrum of one of the present vitamin $B_{12}$ derivatives, $CN-B_{12}(C_{11}CO)$.

The absorption spectrum (300 to 640 nm) of this substance is shown in FIG. 2. Other derivatives showed similar absorption spectra.

EXAMPLE 2

Figure 3:
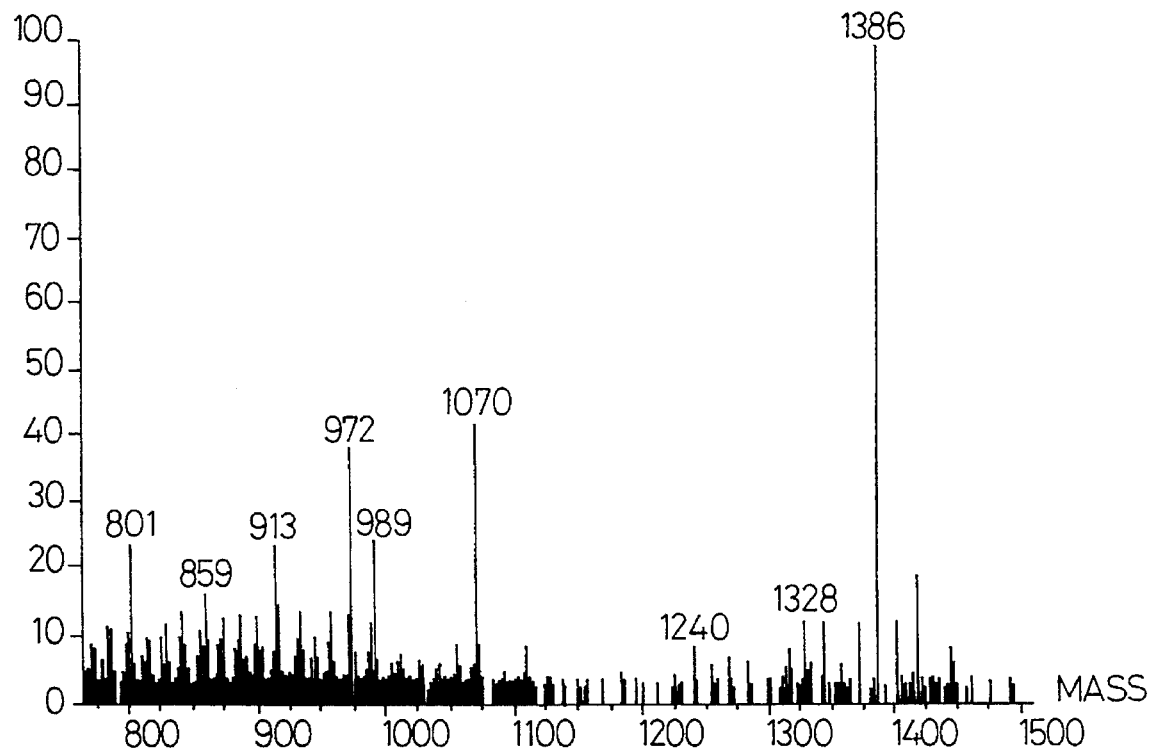
FIG. 3 represents a FAB-MS spectrum of one of the present vitamin $B_{12}$ derivatives, $CN-B_{12}(C_2CO)$.

Similarly as in Example 1, CN-$B_{12}(C_2CO)$, CN-$B_{12}(C_9CO)$, CN-$B_{12}(C_{11}CO)$, and CN-$B_{12}(C_{17}CO)$ were produced. A FAB-MS spectrum of CN-$B_{12}(C_2CO)$ is shown in FIG. 3. Molecular ion was not observed, and a peak of m/e 1386 was assigned to a fragment ion formed by liberating cyan. For CN-$B_{12}$, molecular ion was not observed and similar fragmentation was observed.

EXAMPLE 3

Assay of activity using *E. coli*

Figure 4:
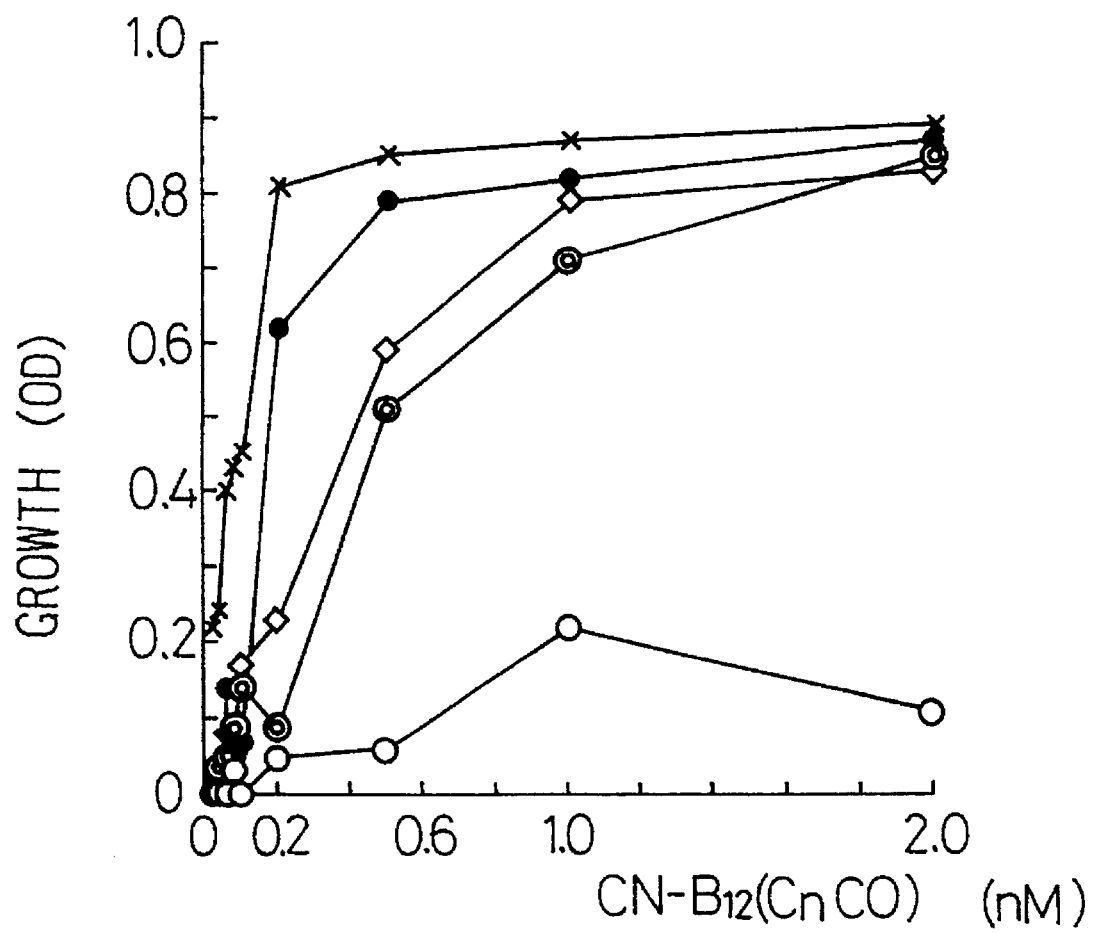
FIG. 4 represents an activity of the present vitamin $B_{12}$ derivatives in E. coli.

To 4.8 ml of an assay medium, 10 μl of a solution of CN-$B_{12}(CnCO)$ in 70% aqueous ethanol was added, and 2 drops of a cell suspension of *E. coli* 215 were added thereon. The mixture was incubated at 37° C. for 16 hours by static culture. The amount of growth of *E. coli* 215 was measured by a spectrophotometer. The result is shown in FIG. 4. The reason why CN-$B_{12}(C_9CO)$ among the acylated vitamin $B_{12}$ derivatives is the best seemed to be because its length of the carbon chain of R is optimum.

It is clear that the present vitamin $B_{12}$ derivatives have physiological activity.

We claim:

1. A vitamin $B_{12}$ derivative represented by the formula:

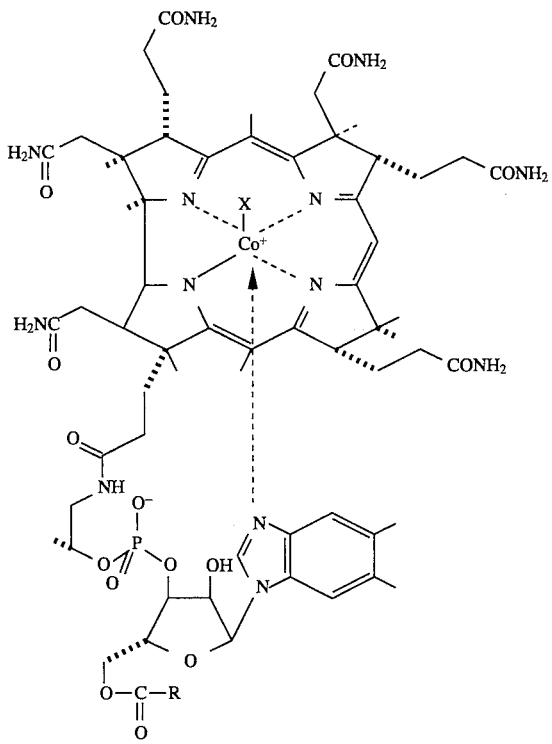

wherein R represents an alkyl group having 2 to 17 carbon atoms, and X represents a cyano group, an alkyl group, or a hydroxyl group.

* * * * *